(12) United States Patent
Schoepgens et al.

(10) Patent No.: US 10,335,352 B2
(45) Date of Patent: Jul. 2, 2019

(54) CREAM-TYPE HAIR COLORING AGENT

(71) Applicant: Henkel AG & Co. KGaA, Duesseldorf (DE)

(72) Inventors: Juergen Schoepgens, Schwalmtal (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 44 days.

(21) Appl. No.: 15/826,685

(22) Filed: Nov. 30, 2017

(65) Prior Publication Data

US 2018/0168942 A1    Jun. 21, 2018

(30) Foreign Application Priority Data

Dec. 19, 2016 (DE) .................. 10 2016 225 380

(51) Int. Cl.
| | | |
|---|---|---|
| *A61Q 5/10* | (2006.01) | |
| *A61K 8/04* | (2006.01) | |
| *A61K 8/34* | (2006.01) | |
| *A61K 8/41* | (2006.01) | |
| *A61K 8/46* | (2006.01) | |
| *A61K 8/81* | (2006.01) | |
| *A61K 8/39* | (2006.01) | |
| *A61K 8/42* | (2006.01) | |
| *A61K 8/86* | (2006.01) | |
| *A61K 8/92* | (2006.01) | |

(52) U.S. Cl.
CPC .............. *A61K 8/042* (2013.01); *A61K 8/342* (2013.01); *A61K 8/39* (2013.01); *A61K 8/41* (2013.01); *A61K 8/42* (2013.01); *A61K 8/463* (2013.01); *A61K 8/8147* (2013.01); *A61K 8/8152* (2013.01); *A61K 8/86* (2013.01); *A61K 8/922* (2013.01); *A61Q 5/10* (2013.01); *A61K 2800/4324* (2013.01); *A61K 2800/882* (2013.01)

(58) Field of Classification Search
CPC ............ A61Q 5/10; A61K 8/342; A61K 8/41; A61K 2800/4324; A61K 2800/882; A61K 8/8152; A61K 8/463; A61K 8/992; A61K 8/8164

See application file for complete search history.

(56) References Cited

U.S. PATENT DOCUMENTS

| | | | |
|---|---|---|---|
| 2002/0010970 A1* | 1/2002 | Cottard | A61K 8/342 8/405 |
| 2008/0199420 A1 | 8/2008 | Wendel et al. | |
| 2012/0285479 A1* | 11/2012 | Zirwen | A61K 8/046 132/208 |

OTHER PUBLICATIONS

Intellectual Property Office, Search Report under Section 17(5) for United Kingdom Patent Application No. GB1719931.6 dated Sep. 20, 2018.

* cited by examiner

*Primary Examiner* — Eisa B Elhilo
(74) *Attorney, Agent, or Firm* — Lorenz & Kopf, LLP

(57) ABSTRACT

The subject of the present disclosure is agents for oxidative hair coloring containing from about 70 about 95 wt. % water, oxidation dye precursor(s), alkalizing agent, from about 0.1-about 2 wt. % anionic, zwitterionic or amphoteric surfactant, and a mixture of sodium polyacrylate, cross-linked copolymers of acrylic acid and non-ethoxylated esters of acrylic acid with linear $C_{10}$-$C_{30}$-monoalcohols, branched $C_{10}$-$C_{50}$-alcohol and linear, saturated $C_8$-$C_{22}$-alkan-1-ol, wherein the dye receives optimal viscosity for application and the consistency of a cream-like gel with outstanding haptics.

19 Claims, No Drawings

CREAM-TYPE HAIR COLORING AGENT

CROSS-REFERENCE TO RELATED APPLICATION

This application claims priority to German Patent Application No. 10 2016 225 380.8, filed Dec. 19, 2016, which is incorporated herein by reference in its entirety.

TECHNICAL FIELD

The present disclosure relates to an oxidative hair coloring agent in cream form, a kit including of this coloring agent and a hair coloring method using this coloring agent.

BACKGROUND

To achieve permanent, intense colors with corresponding fastness properties, so-called oxidative dyes are used. Said dyes usually contain oxidative dye precursors, so-called developer components and coupler components. The developer components join together or couple with one or more coupler components to form, under the influence of oxidants or atmospheric oxygen, the actual colorants per se. Indeed, the oxidative dyes are exemplified by outstanding, long-lasting color results. To achieve natural-looking colors, however, a mix from a large number of oxidative dye precursors must normally be used; in many cases, substantive dyes are still used to create for shading.

Oxidative dyes for stabilization of dye precursors during storage and to accelerate reaction during the oxidative use usually have an alkaline pH value that is adjusted with alkalizing agents, such as alkanolamines, ammonia or inorganic bases.

In order to form the dye, the alkaline coloring component is usually mixed with an aqueous hydrogen peroxide solution to form a homogeneous cream or a homogeneous gel and applied to the hair to be dyed immediately thereafter. This dye mixture remains on the air for a period of from about 5 to about 60 minutes until the oxidative formation of the dye on the hair is complete. Then the dye mixture is washed out.

The aforementioned oxidation dye precursors and alkalizing agents are normally incorporated into a cosmetically suitable carrier, such as a cream. The carrier guarantees homogeneous distribution and an adequate dwell time of the hair coloring agent on the hair. Normal creams contain larger quantities of fat components with a melting point of at least 35° C. as a consistency enhancer. The elaborate production of such creams is disadvantageous. A large amount of energy is required for the melting of the fat components and the emulsification. The subsequent cooling requires large quantities of cooling water.

Another disadvantage is that a cream is relatively expensive to package. Due to their higher viscosity, most creams are not capable of flowing can cannot be transferred from a storage bottle to the application bottle in which the hydrogen peroxide solution is already provided. Instead, the alkaline dye creams are primarily packaged in flexible aluminum tubes, a packaging material that requires high energy and raw material consumption.

A higher viscosity of the dye creams that contain larger quantities of fat components with a melting point of at least 35° C. than consistency enhancer is a further disadvantage in regard to the production of the application mixture. For this purpose, the alkaline dye component is mixed with the developer preparation by hand, e.g. by shaking in a mixing container or by stirring in a mixing bowl. The application mixture must be as homogeneous as possible for a good dyeing result. This mixture should be producible as quickly as possible, because the oxidation dye precursors begin to react immediately on contact with the hydrogen peroxide and oxygen in the air. The application mixture should be so viscous that it remains on the hair and does not drip during the application period described above. For simple production of the application mixture, it would actually be advisable if the alkaline coloring component has only a low viscosity or is only slightly thickened. Furthermore, many consumers prefer a coloring agent having a cream-like nature, since this is perceived as having an especially caring effect for the hair.

BRIEF SUMMARY

Agents for oxidative hair coloring, packaging units (kit-of-parts) including the agents, and methods for oxidative hair coloring using the agents are provided herein. In an embodiment, an agent includes water, at least one oxidation dye precursor, at least one alkalizing agent, at least one surfactant, at least one crosslinked copolymer, at least one branched alkanol having a hydroxyl group and from about 10 to about 50 carbon atoms, at least one linear, saturated 1-alkanol with a hydroxy group and from about 8 to about 22 carbon atoms, and sodium polyacrylate. The at least one surfactant is selected from anionic, zwitterionic and amphoteric surfactants and mixtures thereof. The at least one crosslinked polymer is composed of acrylic acid and non-ethoxylated esters of acrylic acid with linear $C_{10}$-$C_{30}$-mono-alcohols as monomers. Relative to the weight of the agent in each case, the agent includes the water in an amount of from about 70 to about 95 wt. %, the at least one surfactant in a total quantity of from about 0.1-about 2 wt. %, the at least one crosslinked copolymer in a total amount of from about 0.05-about 2 wt. %, and the at least one linear, saturated 1-alkanol with a hydroxy group and from about 8 to about 22 carbon atoms in a total amount of from about 0.1-about 1.5 wt. %. No additional fat components with a melting point of 35° C. or higher in addition to the obligatory ingredients mentioned above are included in the agent. No saturated and unsaturated alkane carboxylic acids with from about 1 to about 50 carbon atoms are included in the agent. No oxidants are included in the agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The task of the present disclosure is to provide an oxidative hair coloring agent that can be produced under the most economical and sustainable conditions. Furthermore, the task of the present disclosure was to provide an oxidative hair coloring agent that can be packaged under the most economical and sustainable conditions possible. Furthermore, the task of the present disclosure was to provide an oxidative hair coloring agent that can be mixed and applied easily.

Furthermore, the task of the present disclosure was to provide an oxidative hair coloring agent that has a cream-like consistency, haptics and appearance without a high content of higher-melting fat components.

These tasks are achieved with an agent for oxidative hair coloring which, in relation to its weight, contains the following:
- from about 70-about 95 wt. % water,
- at least one oxidation dye precursor,
- at least one alkalizing agent,
- at least one surfactant selected from anionic, zwitterionic and amphoteric surfactants and mixtures thereof, in a total amount of from about 0.1-about 2 wt. %,
- at least one crosslinked copolymer composed of acrylic acid and non-ethoxylated esters of acrylic acid with linear $C_{10}$-$C_{30}$ monoalcohols as monomers, wherein the crosslinked copolymer is present in a total amount of from about 0.05 to about 2 wt. %,
- at least one branched alkanol having a hydroxyl group and from 10 to about 50 carbon atoms, preferably in a total amount of from about 0.1-about 5 wt. %, preferably from about 0.4-about 4 wt. %, more preferably from about 0.7-about 3 wt. %, particularly from about 1-about 2 wt. %, in each case relative to the weight of the agent,
- at least one linear, saturated 1-alkanol with a hydroxy group and from 8 to about 22 carbon atoms in a total amount of from about 0.1-about 1.5 wt. %, preferably from about 0.3-about 1 wt. %, particularly from about 0.5-about 0.8 wt. %, wherein
- no additional fat components with a melting point of 35° C. or higher in addition to the obligatory ingredients mentioned above,
- no saturated and unsaturated alkane carboxylic acids with from 1 to about 50 carbon atoms and
- no oxidants are contained, exemplified in that sodium polyacrylate, preferably having a mass-average molar mass $M_w$ in the range from about 1,000,000 to about 20,000,000 daltons, preferably from about 6,000,000 to about 15,000,000 daltons, preferably in a total amount of from about 0.1-about 1.5 wt. %, more preferably from about 0.5-about 1.3 wt. %., particularly from about 0.8-about 1.1 wt. %, relative to weight of the agent on each case, wherein use of sodium polyacrylate is particularly preferred as pre-gelled in a water-in-oil emulsion.

The agent as contemplated herein is an alkaline dye component of an oxidative hair coloring agent. This is normally mixed with an aqueous hydrogen peroxide preparation immediately before application and then applied to the hair to be dyed. The agent as contemplated herein does not have any oxidants until it is mixed with the aqueous hydrogen peroxide preparation.

Water Content

The agent as contemplated herein contains from about 70-about 95 wt. % water, preferably from about 78-about 91 wt. % water, relative to its weight in each case.

Alkalizing Agent

The agent as contemplated herein contains at least one alkalizing agent. The pH value preferred for adjustment of the alkalizing agent preferred as contemplated herein is selected from the group of ammonium hydroxide, basic amino acids, alkali metal hydroxides, alkanolamines, alkali metal metasilicates, alkali metal phosphates and mixtures thereof. Lithium, sodium and potassium, particularly sodium or potassium are preferred for use as alkali metal ions.

Preference is given to the basic amino acids which can be used as alkalizing agents selected from the group l-arginine, d-arginine, d,l-arginine, l-lysine, d-lysine, d,l-lysine, particularly preferably l-arginine, d-arginine, d,l-arginine and used as an alkalizing agent as contemplated herein.

The alkali hydroxides which can be used as alkalizing agents are preferably selected from sodium hydroxide and potassium hydroxide.

The alkanolamines used as an alkalization agent are preferably selected from primary amines with a $C_2$-$C_6$-alkyl base body having at least one hydroxyl group. It is particularly preferable that alkanolamines are selected from the group comprising 2-aminoethan-1-ol (monoethanolamine), 3-aminopropan-1-0l, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. As contemplated herein, it is most preferable that alkanolamines are selected from the group of 2-aminoethan-1-ol, 2-amino-2-methylpropan-1-ol and 2-amino-2-methylpropan-1,3-diol.

A particularly preferred alkalizing agent as contemplated herein is a monoethanolamine (2 aminoethan-1-ol). In order to achieve a coloring method that is as odor-free as possible and to optimize the authenticity properties of the coloring, monoethanolamine is used in a total amount of from about 0.2 to about 10 wt. %, preferably from about 0.5 to about 8 wt. %, more preferably from about 1 to about 6 wt. % and particularly from about 2 to about 4 wt. %, relative to the weight of the coloring agent as contemplated herein. Additional preferred coloring agents as contemplated herein contain ammonium hydroxide, i.e. ammonia in the form of its aqueous solution, in addition to or instead of monoethanolamine The corresponding aqueous ammonia solutions can be from about 10 to about 35% solutions, calculated in vol. % of 100 g aqueous ammonia solution containing 25% by volume of $NH_3$ and about 50 g of ammonia. Ammonia in the form of a from about 20 to about 30 vol. % solution is preferably used, particularly in the form of a 25 vol. % solution.

In an especially preferred embodiment, the coloring agent as contemplated herein contains ammonium hydroxide in an amount from about 0.2 to about 6 wt. %, preferably from about 0.4 to about 5 wt. %, more preferably from about 1.0 to about 3 wt. % and particularly from about 0.3 to about 1.5 wt. %, relative to the weight of the coloring agent as contemplated herein.

Furthermore, other alkalizing agents, such as potassium hydroxide and sodium hydroxide can be included, preferably in a total amount of from about 0.05 to about 1.5 Wt. %, preferably from about 0.1 to about 0.6 wt. %, relative to the weight of the coloring agent as contemplated herein in each case.

In an additional particularly preferred embodiment, the coloring agent as contemplated herein contains at least one alkalizing agent in a total amount of from about 0.02-about 0.4 mol/100 G, preferably from about 0.05-about 0.3 mol/100 g, in one mol of alkalizing agent per 100 grams of the agent as contemplated herein in each case.

Preferred agents as contemplated herein are exemplified by a pH value in the range of from about 8-about 12, preferably from about 9-about 11.5, particularly from about 9.5-about 10.5, measured at 20° C. in each case.

Anionic, Zwitterionic or Amphoteric Surfactant

The agent as contemplated herein contains at least one surfactant selected from anionic, zwitterionic and amphoteric surfactants and mixtures thereof, in a total amount of from about 0.1-about 2 wt. %, preferably from about 0.3-about 1.5 wt. % and particularly from about 0.5-about 1.2 wt. %, relative to the weight of the agent in each case.

Surfactants and emulsifiers according to the present application are amphiphilic (bifunctional) compounds, which include at least one hydrophobic and at least one hydrophilic molecular part.

In the context of the present disclosure, saturated and unsaturated alkan-1-ols having at least 4 carbon atoms in the alk(en)yl radical, alkane carboxylic acids having at least 4 carbon atoms in the alk(en)yl radical and glyceryl fatty acid mono- and diesters having at least 4 carbon atoms in the fatty acid radical are not counted among the surfactants.

The hydrophobic radical is preferably a hydrocarbon chain with from 8-about 30 carbon atoms, which can be saturated or unsaturated, linear or branched. This $C_8$-$C_{30}$ alkyl chain is most preferably linear. Basic properties of the surfactants and emulsifiers are the oriented absorption at boundary surfaces, as well as the aggregation to micelles and the formation of lyotropic phases.

With selection of suitable surfactants in the context of the present disclosure, it may be preferable to use a mixture of surfactants in order to optimally adjust the properties of the oxidizing coloring agent as contemplated herein can be preferable.

Suitable anionic surfactants for the agents as contemplated herein are all anionic surfactant substances suitable for use on the human body, which contain a water-solubilizing anionic group, for example a sulfate, sulfonate or phosphate group, and a lipophilic alkyl group having about from 8 to about 30 carbon atoms, preferably from 8 to about 24 carbon atoms in the molecule, with the exception of linear and branched fatty acids having from 8 to about 30 carbon atoms and salts thereof (soaps). Furthermore, the molecule can contain glycol or polyglycol ether groups, ester, ether and amide groups, as well as hydroxyl groups. Examples of suitable anionic surfactants are, each in the form of sodium, potassium and ammonium salts, as well as mono-, di- and trialkanol ammonium salts having from 2 to 4 carbon atoms in the alkanol group, polyethoxylated ether carboxylic acids, acylsarcosides, acyltaurides, acyl isethionates, sulfosuccinic acid mono- and dialkyl esters and sulfosuccinic acid monoalkyl polyoxyethyl esters with 1 to 6 ethylene oxide groups, linear alkane sulfonates, linear alpha-olefin sulfonates, sulfonates of unsaturated fatty acids having up to 6 double bonds, alpha-sulfofatty acid methyl esters of fatty acids, $C_8$-$C_{20}$-alkyl sulfates and $C_8$-$C_{20}$-alkyl ether sulfates having from 1 to 15 oxyethyl groups, mixtures of surfactant hydroxysulfonates, sulfated hydroxyalkyl polyethylene and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, and monoglyceride sulfates and monoglyceride ether sulfates. Preferred anioinic surfactants are selected from $C_8$-$C_{20}$-alkyl sulfates, $C_8$-$C_{20}$-alkyl ether sulfates and $C_8$-$C_{20}$-ether carboxylic acids, each having from 8 to about 20 carbon atoms in the alkyl group and from 0 to 12 ethylene oxide groups in the molecule. Sodium laureth(2) sulfate is particularly preferred.

Surfactant combinations containing a lipophilic alkyl group with from 8 to about 30 carbon atoms, preferably from 8 to about 24 carbon atoms and at least one quaternary ammonium group and at least one carboxylate, sulfonate or sulfate group are identified as zwitterionic surfactants. Particularly suitable zwitterionic surfactants are the so-called betaines such as n-alkyl-n, n-dimethylammonium glycinates, for example coco-alkyldimethyl ammonium glycinate, n-acylaminopropyl-n, n-dimethyl ammonium glycinates, for example coco-acylaminopropyldimethyl ammonium glycinate (with the INCI designation cocamidopropyl betaine), and 2-alkyl-3-carboxymethyl-3-hydroxyethyl imidazolines each having from 8 to 18 carbon atoms in the alkyl or acyl group and coco-acylaminoethylhydroxyethyl carboxymethyl glycinate, as well as sultaines or sulfobetaines. A preferred zwitterionic surfactant is the cocoacylaminopropyl dimethyl ammonium glycinate known by the INCI designation cocamidopropyl betaine.

Amphoteric surfactants are also understood to mean surfactant compounds which contain a $C_8$-$C_{30}$ alkyl or acyl group and at least one free amino group and at least one —COOH or —$SO_3H$ group in the molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case from 8 to about 30 carbon atoms in the alkyl group. Particularly preferred amphoteric surfactants are N cocosalkylaminopropionate, cocosacylaminoethylaminopropionate and $C_{12}$-$C_{18}$ acylsarcosin.

Anionic or zwitterionic surfactants preferred as contemplated herein are selected from $C_8$-$C_{20}$ alkyl sulfates, $C_8$-$C_{20}$-alkyl ether sulfates and $C_8$-$C_{20}$-ether carboxylic acids, each having from 8 to about 20 carbon atoms in the alkyl group and from 0 to 12 ethylene oxide groups in the molecule, wherein sodium laureth(2)sulfate is particularly preferred, furthermore from coconut acylaminopropyl dimethyl ammonium glycinate, and from mixtures of these surfactants.

Agents particularly preferred as contemplated herein contain at least one anionic or zwitterionic surfactant selected from $C_8$-$C_{20}$ alkyl sulfates, $C_8$-$C_{20}$ alkyl ether sulfates and $C_8$-$C_{20}$ ether carboxylic acids, each having from 8 to about 20 carbon atoms in the alkyl group and from 0 to 12 ethylene oxide groups in the molecule, wherein sodium laureth(2) sulfate is particularly preferred, furthermore from coconut acylaminopropyl dimethyl ammonium glycinate, and from mixtures of these surfactants, in a total amount of from about 0.1-about 2 wt. %., preferably from about 0.3-about 1.5 wt. %, and particularly from about 0.5-about 1.2 wt. %, based in each case on the weight of the agent.

A further essential feature of the agents as contemplated herein is the content of at least one crosslinked copolymer, composed of acrylic acid and non-ethoxylated esters of acrylic acid with linear $C_{10}$-$C_{30}$-monoalcohols as monomers, wherein the crosslinked copolymer is present in a total amount of from about 0.05-about 2 wt. %, preferably from about 0.1-about 1.5 wt. %, more preferably from about 0.3-about 1 wt. %, particularly from about 0.5-about 0.8 wt. %, relative to the weight of the agent in each case. The at least one crosslinked copolymer is preferably selected from acrylic acid and non-ethoxylated esters of acrylic acid with linear $C_{10}$-$C_{30}$-monoalcohols selected from copolymers having the INCI name acrylates/$C_{10\text{-}30}$ alkyl acrylate crosspolymer. Sucrose allyl ether or pentaerythrityl allyl ether is preferably contained as a crosslinking agent.

As contemplated herein, particularly preferred crosslinked copolymers of acrylic acid and non-ethoxylated esters of acrylic acid with linear $C_{10}$-$C_{30}$-monoalcohols can be obtained by polymerization of a monomer mixture containing from about 80 to about 99 wt. %, preferably from about 90 to about 98 wt. % acrylic acid, at least one non-ethoxylated ester of acrylic acid with linear $C_{10}$-$C_{30}$-monoalcohols in a total amount of from about 0.9-about 19.9 wt. %, preferably from about 2-about 10 wt. % and at least one crosslinking agent in a total amount of from about 0.1-about 4 wt. %, relative to the weight of the monomer mixture.

Further preferred crosslinked polymers of acrylic acid and non-ethoxylated esters of acrylic acid with linear $C_{10}$-$C_{30}$ monoalcohols as contemplated herein are exemplified in that their 0.5 wt. % dispersion in water at 25° C. and a pH value in the range of from about 5.8-about 6.3 has a viscosity in the range of from about 45,000 to about 65,000 mPas, measured with a Brookfield RVF or Brookfield RVT viscosimeter with a rotation frequency of 20 rpm with spindle #7.

Furthermore, the agents as contemplated herein and agents used as contemplated herein contain at least one branched alkanol with a hydroxy group and from 10 to about 50 carbon atoms. In the context of the present disclosure, at least one branched alcohol with a hydroxy group and from 10 to about 50 carbon atoms selected from 2 hexyldecanol, 2-ocyltdodecanol, 2-ethylhexylalcohol and isostearylalcohol, as well as mixtures thereof is preferable. As contemplated herein, 2-octyldodecanol is particularly preferable. Particularly preferred agents or particularly preferred agents used as contemplated herein are exemplified in that at least one branched alkanol having a hydroxyl group and from 10 to about 50 carbon atoms, preferably in a total amount of from about 0.1-about 5 wt. %, preferably from about 0.4-about 4 wt. %, more preferably from about 0.7-about 3 wt. %, particularly from about 1-about 2 wt. %, in each case relative to the weight of the agent, is contained. As contemplated herein, extraordinarily preferred or preferably used agents are exemplified in that from about 0.1-about 5 wt. %, preferably from about 0.4-about 4 wt. %, more preferably from about 0.7-about 3 wt. %, particularly from about 1-about 2 wt. % 2-octyldodecanol, relative to the weight of the agent in each case, is contained.

Furthermore, the agents as contemplated herein and agents used as contemplated herein contain at least one linear, saturated 1-alkanol with a hydroxy group and from 8 to about 22 carbon atoms in a total amount of from about 0.1-about 1.5 wt. %, preferably from about 0.3-about 1 wt. %, particularly from about 0.5-about 0.8 wt. %, relative to the weight of the agent in each case. As contemplated herein, it is preferable that at least one linear, saturated 1-alkanol with a hydroxy group and from 8 to about 22 carbon atoms selected from 1-decanol, 1-dodecanol (lauryl alcohol), 1-tridecanol, 1-tetradecanol (myristylalcohol), 1-hexadecanol (cetyl alcohol), 1-octadecanol (stearyl alcohol) and 1-eicosanol (arachyl alcohol), as well as mixtures thereof. A particularly preferred alkanol mixture as contemplated herein is coconut alcohol, i.e. alkanol mixtures that are obtained by employing hydrogenation of coconut oil. Particularly preferred coconut alcohol as contemplated herein has the following chain length distribution, relative to its weight in each case: C10 and shorter: from about zero to about 3 wt. %, C12: from about 48-about 58 wt. %, C14: from about 18-about 24 wt. %, C16: from about 8-about 12 wt. %, C18: from about 11-about 15 wt. %, C20: from about zero to about 1 wt. %. Additional particularly preferred $C_8$-$C_{22}$-alkan-1-ols are selected from 1-dodecanol (lauryl alcohol), 1-tetradecanol (myristyl alcohol) and mixtures thereof.

Furthermore, the agents as contemplated herein do not contain any saturated and unsaturated alkane carboxylic acids with from 1 to about 50 carbon atoms, particularly no oleic acid.

Furthermore, in addition to the mandatory ingredients mentioned above—i.e. apart for the linear, saturated 1-alkanols with a hydroxy group and from 8 to about 22 carbon atoms—, the agents as contemplated herein contain no additional fat components having a melting point of 35° C. and above. The melting point specification relates to a pressure of 1013 mbar, as is also the case for the specifications of other physical measurement values in this application. These fat components having a melting point of 35° C. and higher include, in particular, natural vegetable waxes, for example, candelilla wax, carnauba wax, Japan wax, sugar cane wax, ouricury wax, cork wax, sunflower wax, fruit waxes such as orange waxes, lemon waxes, grapefruit wax, and animal waxes, such as beeswax, shellac wax and spermaceti, further montane ester waxes, hydrogenated jojoba waxes and sasol waxes, polyalkylene waxes, polyethylene glycol waxes, $C_{20}$-$C_{40}$-dialkyl esters of dimer acids, $C_{30-50}$-alkyl beeswax, alkyl and alkylaryl esters of dimer fatty acids, esters of a saturated, monohydric, preferably linear, $C_{16}$-$C_{60}$-alcohol and a saturated, preferably linear, $C_8$-$C_{36}$-monocarboxylic acid, such as, for example, cetyl palmitate, myristyl myristate, cetyl behenate and stearyl behenate, additionally, triglycerides of saturated and optionally hydroxylated $C_{12-30}$-fatty acids, such as hardened triglyceride fats (hydrogenated palm oil, hydrogenated coconut oil, hydrogenated castor oil), glyceryl tribehenate (tribehin) or glyceryl tri-12-hydroxystearate.

The agents as contemplated herein and agents used as contemplated herein are exemplified in that they contain sodium polyacrylate. As contemplated herein, sodium polyacrylate is preferably understood to mean polymers having the CAS number 9003-04-7. Preferred sodium polyacrylates as contemplated herein have an average molar mass $M_w$ in the range from about 1,000,000 to about 20,000,000 daltons, preferably from about 6,000,000 to about 15,000,000 daltons. The average molecular weight $M_w$ can, for example, be determined by employing gel permeation chromatography (GPC) with polystyrol as an internal standard in accordance with DIN 55672-3, version 8/2007.

The mixture of sodium polyacrylate, crosslinked copolymers of acrylic acid and non-ethoxylated esters of acrylic acid with linear $C_{10}$-$C_{30}$-monoalcohols, branched $C_{10}$-$C_{50}$-alkanol and linear, saturated $C_8$-$C_{22}$-alkan-1-ol as contemplated herein achieves a thickening of the agent with the optimal viscosity for the application, wherein the agent also has the consistency of a cream-like gel with outstanding haptics.

Preferred agents as contemplated herein contain sodium polyacrylate in a total amount of from about 0.1-about 1.5 wt. %, preferably from about 0.5-about 1.3 wt. %, particularly from about 0.8-about 1.1 wt. %, relative to the weight of the agent in each case.

In an especially preferred embodiment, the sodium polyacrylate is contained as a sodium polyacrylate pre-gelatinized in a water-in-oil emulsion. In the process, it is especially preferred that the water-in-oil emulsion containing sodium polyacrylate contains from about 40-about 60 wt. % sodium polyacrylate, a total of from about 25-about 45 wt. % oil(s), a total of from about 0.5-about 4.9 wt. % surfactant(s) and from about 0.5-about 4.9 wt. % water, relative to its weight.

It is particularly preferable that the oil contained in the water-in-oil emulsion containing sodium polyacrylate is selected from natural and synthetic hydrocarbons, particularly preferably from mineral oil, paraffin oils, $C_{18}$-$C_{30}$-isoparaffins, particularly isoeicosane, polyisobutenes and polydecenes, $C_8$-$C_{16}$ isoparaffins, and 1,3-di (2-ethylhexyl)-cyclohexane; the benzoic esters of linear or branched $C_{8-22}$-alkanols; triglycerides of linear or branched, saturated or unsaturated, optionally hydroxylated $C_{8-30}$-fatty acids, in particular natural oils; the dicarboxylic acid esters of linear or branched $C_2$-$C_{10}$-alkanols; the esters of the linear or branched saturated or unsaturated fatty alcohols having from 2 to about 30 carbon atoms with linear or branched saturated or unsaturated fatty alcohols having from 2 to about 30 carbon atoms, which can be hydroxylated; the addition products of 1 to 5 propylene oxide units to mono- or polyhydric $C_{8-22}$-alkanols; the $C_8$-$C_{22}$-fatty alcohol esters of monohydric or polyhydric $C_2$-$C_7$-hydroxycarboxylic acids; the symmetrical, asymmetric or cyclic esters of carbonic acid with $C_{3-22}$-alkanols, $C_{3-22}$-alkane diols or $C_{3-22}$-alkane triols; the esters of dimeric unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols; silicone oils and mixtures of the aforementioned substances. A particularly preferred oil as contemplated herein is mineral oil.

It is especially preferred that the water-in-oil emulsion containing sodium polyacrylate contains surfactant selected from nonionic surfactants. Particularly preferred non-ionic surfactants are selected from 7-about 80 mol of ethylene oxide per mole of ethoxylated castor oil, ethoxylated $C_8$-$C_{24}$-alkanols with from 5-about 30 mol of ethylene oxide per mole, ethoxylated $C_8$-$C_{24}$-carboxylic acids with from 5-about 30 mol of ethylene oxide per mole, with 4-50 mol of ethylene oxide per mole of ethoxylated sorbitan monoesters of linear saturated and unsaturated $C_{12}$-$C_{30}$-carboxylic acids, which can be hydroxylated, in particular those of myristic acid, palmitic acid, stearic acid or mixtures of these fatty acids, alkyl mono- and oligoglycosides having from 8 to about 22 carbon atoms in the alkyl radical and their ethoxylated analogs, and mixtures of the aforementioned substances.

The ethoxylated $C_8$-$C_{24}$-alkanols have the formula $R^1O(CH_2CH_2O)_nH$, wherein $R^1$ denotes a linear or branched alkyl and/or alkenyl radical with from 8-about 24 carbon atoms and n, the average number of ethylene oxide units per molecule, for integers from 5-about 30, preferably from 6-about 20, particularly from 6 to 12 mol of ethylene oxide on 1 mol of caprylic alcohol, 2-ethylhexyl alcohol, capric alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, and technical mixtures thereof. Adducts of from 10 to about 100 mol of ethylene oxide with technical fatty alcohols having from 12 to 18 carbon atoms are also known, such as coconut, palm, palm kernel or tallow fatty alcohol, are suitable. Particular preference is given to trideceth-6, isotrideceth-6, undeceth-6, myreth-6, laureth-10, laureth-12, laureth-15, laureth-20, laureth-30, myreth-10, myreth-12, myreth-15, myreth-20, myreth-30, ceteth-10, ceteth-12, ceteth-15, ceteth-20, ceteth-30, steareth-10, steareth-12 steareth-15, steareth-20, steareth-30, oleth-10, oleth-12, oleth-15, oleth-20, oleth-30, ceteareth-10, ceteareth-15, ceteareth-12, ceteareth-15, ceteareth-20, ceteareth-30 and coceth-10, coceth-12, coceth-15, coceth-20 and coceth-30; trideceth-6 and isotrideceth-6 and mixtures thereof.

The ethoxylated $C_8$-$C_{24}$-carboxylic acids have the formula $R^1O(CH_2CH_2O)_nH$, wherein $R^1O$ denotes a linear or branched saturated or unsaturated alkenyl radical with from 8-about 24 carbon atoms and n, the average number of ethylene oxide units per molecule, for integers from 5-about 30, preferably from 6-about 20, particularly from 6 to 12 mol of ethylene oxide on 1 mol of caprylic alcohol, 2-ethylhexanoic acid, capric acid, lauric acid, isotridecanoic acid, myristic acid, cetyl acid, palmitoleic acid, stearic acid, isostearic acid, oleic acid, elaidic acid, petroselinic acid, arachidic acid, gadoleic acid, behenic acid, erucic acid and brassidic acid, and technical mixtures thereof. Adducts of from 5-about 30 mol, preferably from 6-about 20 mol, particularly from 6-12 mol of ethylene oxide with technical fatty acids having from 12 to 18 carbon atoms, such as coconut, palm, palm kernel or tallow fatty alcohol, are suitable.

As contemplated herein, particularly preferred agents are exemplified in that they comprise at least one sodium polyacrylate having an average molar mass $M_w$ in the range from about 1,000,000 to about 20,000,000 daltons, preferably from about 6,000,000 to about 15,000,000 daltons, in a total amount of from about 0.1 to about 1.5 wt. %, preferably from about 0.5 to about 1.3 wt. %, particularly from about 0.8-about 1.1 wt. %, relative to the weight of the agent in each case, wherein the sodium polyacrylate is present as pre-gelled in a water-in-oil emulsion, wherein said water-in-oil emulsion, is from about 40-about 60 wt. % sodium polyacrylate, in total from about 25-about 45 wt. % oil(s), preferably mineral oil, in total from about 0.5-about 4.9 wt. % surfactant(s), preferably from about 0.5-about 4.9 wt. % non-ionic surfactant (E), and from about 0.5-about 4.9 wt.-% water, relative to their weight in each case.

Agents preferred or used as contemplated herein have a viscosity in the range of from about 5000-about 40,000 mPas, preferably from about 6000-about 30,000 mPas, particularly from about 7500-about 20000 mPas, in each case measured at 20° C. using a rotational viscometer (Haake VT 550) at a rotational frequency of $7.2\ s^{-1}$ with the measurement geometry SV.

As contemplated herein, preferred and preferably used agents contain, in addition to the at least one branched alkanol having a hydroxyl group and from about 10 to about 50 carbon atoms, at least one additional oil in a total amount of from about 0.2-about 6 wt. %, preferably from about 0.5-about 5 wt. %, particularly from about 0.7-about 3 wt. %, relative to the weight of said agent in each case, wherein these quantities include the oils from the preferred sodium polyacrylate emulsion as contemplated herein. This additional oil can be selected from the same oils that can also be comprised in the sodium polyacrylate emulsions preferred as contemplated herein. It is preferable that the at least one additional is selected from natural and synthetic hydrocarbons, particularly preferably from mineral oil, paraffin oils, $C_{18}$-$C_{30}$-isoparaffins, particularly isoeicosane, polyisobutenes and polydecenes, $C_8$-$C_{16}$ isoparaffins, and 1,3-di(2-ethylhexyl)-cyclohexane; the benzoic esters of linear or branched $C_{8-22}$-alkanols; triglycerides of linear or branched, saturated or unsaturated, optionally hydroxylated $C_{8-30}$-fatty acids, in particular natural oils; the dicarboxylic acid esters of linear or branched $C_2$-$C_{10}$-alkanols; the esters of the linear or branched saturated or unsaturated fatty alcohols having from 2 to about 30 carbon atoms, branched saturated or unsaturated fatty acids having from 2 to about 30 carbon atoms, which can be hydroxylated; the addition products of from 1 to 5 propylene oxide units to mono- or polyhydric $C_{8-22}$-alkanols; the $C_8$-$C_{22}$-fatty alcohol esters of monohydric or polyhydric $C_2$-$C_7$-hydroxycarboxylic acids; the symmetrical, asymmetric or cyclic esters of carbonic acid with $C_{3-22}$-alkanols, $C_{3-22}$-alkane diols or $C_{3-22}$-alkane triols; the esters of dimeric unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols; silicone oils and mixtures of the aforementioned substances. As contemplated herein particular preference is given to oils selected from paraffin oils, natural oils, in particular amaranthus seed oil, apricot kernel oil, arganil, avocado oil, babassu oil, cottonseed oil, borage seed oil, cameline oil, safflower oil, peanut oil, pomegranate core oil, grapefruit seed oil, hemp oil, hazelnut oil, palm seed oil, jojoba oil, linseed oil, macadamia nut oil, corn oil, almond oil, marula oil, evening primrose oil, olive oil, palm oil, palm kernel oil, parannut oil, pecknut oil, peach kernel oil, rapeseed oil, castor oil, sandalwood oil, castor oil, sesame oil, soya oil, sunflower oil, grapeseed oil, walnut oil, wild-type oil, wheat germ oil, and the liquid fractions of coconut oil, and also synthetic triglyceride oils, in particular capric/caprylic triglycerides, furthermore the esters of linear or branched saturated or unsaturated fatty alcohols having from 2-about 30 carbon atoms with linear or branched saturated or unsaturated fatty acids having from 2-about 30 carbon atoms, which can be hydroxylated, in particular isopropyl palmitate and isopropyl myristate, and mixtures of the aforementioned oils.

An additional essential feature of the agent as contemplated herein is the content of at least one oxidative dye precursor.

On the basis of their reaction behavior, oxidative dye precursors can be divided into two categories, so-called developer components and coupler components.

In the context of oxidative dyeing, coupler components alone do not form any significant coloration and always require the presence of developer components. Developer components can combine together to form the actual dye.

The developer and coupler components are normally used in a free form. In the case of substances with amino groups, however, use of the salt form, particularly in the form of hydrochlorides and hydrobromides or sulfates, may be preferred.

The oxidation dye precursors include oxidation dye precursors of the developer type and of the coupler type. Particularly suitable oxidation dye precursors of the developer type are selected from at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis (2-hydroxyethyl)-p-phenylenediamine, 2-methoxymethyl-p-phenylenediamine, N-(4-amino-3-methylphenyl)-N-[3-(1H-imidazol-1-yl) propyl]amine, N,N'-bis (2-hydroxyethyl)-N,N'-bis-(4-aminophenyl)-1,3-diamino-propane-2-ol, bis-(2-hydroxy-5-aminophenyl) methane, 1,3-bis(2,5-diaminophenoxy) propan-2-ol, N,N'-bis (4-aminophenyl)-1,4-diazacycloheptane, 1,10-bis (2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H, 5H-pyrazolo[1,2-a]pyrazol-1-on and the physiologically tolerated salts thereof. Particular preference is given to developer components selected from p-toluenediamine, 2-(2-hydroxyethyl)-p-phenylenediamine, n,n-bis-(2-hydroxyethyl)-p-phenylenediamine, 2-methoxymethyl-p-phenylenediamine and/or 4,5-diamino-1-(2-hydroxyethyl)-pyrazole and the physiologically acceptable salts and mixtures thereof.

Particularly suitable oxidation dye precursors of the coupler type are selected from the group of 3-Aminophenol, 5-Amino-2-methylphenol, 3-Amino-2-chlor-6-methylphenol, 2-Hydroxy-4-aminophenoxyethanol, 5-Amino-4-chlor-2-methylphenol, 5-(2-Hydroxyethyl)-amino-2-methylphenol, 2,4-Dichlor-3-aminophenol, 2-Aminophenol, 3-Phenylendiamine, 2-(2,4-Diaminophenoxy)ethanol, 1,3-Bis(2,4-diaminophenoxy)propane, 1-Methoxy-2-amino-4-(2-hydroxyethylamino)benzol, (2-amino-4-[(2-hydroxyethyl)amino]-anisol), 1,3-Bis(2,4-diaminophenyl)propane, 2,6-Bis(2'-hydroxyethylamino)-1-methylbenzol 2-({3-[(2-Hydroxyethyl)amino]-4-methoxy-5-methylphenyl}amino) ethanol, 2-({ 3-[(2-Hydroxyethyl)amino]-2-methoxy-5-methylphenyl}amino)ethanol, 2-({ 3-[(2-Hydroxyethyl) amino]-4,5 dimethylphenyl}amino)ethanol, 2-[3-Morpholin-4-ylphenyl)amino]ethanol, 3-Amino-4-(2-methoxyethoxy)-5-methylphenylamine, 1-Amino-3-bis-(2-hydroxyethyl)aminobenzol, Resorcin, 2-Methylresorcin, 4-Chlorresorcin, 1,2,4-Trihydroxybenzol, 2-Amino-3-hydroxypyridine, 3-Amino-2-methylamino-6-methoxypyridin, 2,6-Dihydroxy-3,4-dimethylpyridin, 3,5-Diamino-2,6-dimethoxypyridin, 1-Phenyl-3-methylpyrazol-5-on, 1-Naphthol, 1,5-Dihydroxynaphthalene, 2,7-Dihydroxynaphthalene, 1,7-Dihydroxynaphthalene, 1,8-Dihydroxynaphthalene, 4-Hydroxyindol, 6-Hydroxyindol, 7-Hydroxyindol, 4-Hydroxyindolin, 6-Hydroxyindolin, 7-Hydroxyindolin or mixtures of these compounds or their physiologically compatible salts. Particular preference is given to coupler components selected from 3-aminophenol, 5-amino-2-methylphenol, 3-amino-2-chloro-6-methylphenol, 2-hydroxy-4-aminophenoxyethanol, 2-(2,4-diaminophenoxy) ethanol, 1-methoxy-2-amino-4-(2-hydroxyethylamino)benzene (2-amino-4-[(2-hydroxyethyl)amino] anisole), resorcinol, 2-methylresorcinol, 4-chlororesorcinol, 2-amino-3-hydroxypyridine, and physiologically acceptable salts thereof, and mixtures thereof.

In a preferred embodiment, the coloring agents as contemplated herein contain one or more oxidation dye precursors in a total amount of from about 0.001 to about 5.0 wt. %, preferably from about 0.01 to about 4.0 wt. %, more preferably from about 0.2 to about 3.5 wt. %, more preferably from about 0.3 to about 2.5 wt. % and particularly from about 0.7 to about 1.8 wt. %, relative to the weight of the dye as contemplated herein and/or the weight of the composition used as contemplated herein (M1).

In a preferred embodiment, the dyes as contemplated herein contain one or multiple oxidation dye precursors selected from at least one developer component and possibly at least one coupler component in a total amount of from about 0.001 to about 5.0 wt. %, preferably from about 0.01 to about 4.0 wt. %, more preferably from about 0.2 to about 3.5 wt. %, more preferably from about 0.3 to about 2.5 wt. % and particularly from about 0.7 to about 1.8 wt. %, relative to the weight of the dye as contemplated herein and/or the weight of the composition used as contemplated herein (M1).

In a further preferred embodiment of the present disclosure, the agent as contemplated herein contains at least one direct dye.

In oxidative hair coloring agents, direct dyes are frequently used for shading undesired red strands, which can be generated by the melanin degradation products, or for shading certain blond shades.

In order to obtain a balanced and usable shade formation, the present disclosure may specify that the cosmetic agents with oxidization dye precursors additionally contains at least one direct dye.

Partially-oxidizing dyes are dyes that coat the substrate itself and do not require an oxidative process to create the color. Partially-oxidizing dyes are usually nitrophenylendiamines, nitroaminophenols, azo dyes, anthraquinones or indophenols.

Partially-oxidizing dyes can be divided between anionic, cationic and non-ionic partially-oxidizing dyes.

Preferred anionic partially-oxidizing dyes are the compounds known under the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromophenole blue.

Preferred cationic partially-oxidizing dyes are cationic triphenylmethane dyes, such as Basic Blue 7, Basic Blue 26, Basic Violet 2 and Basic Violet 14, as well as aromatic systems, which are substituted with a quaternary nitrogen group, such as Basic Yellow 57, Basic Red 76, Basic Blue 99, Basic Brown 16 and Basic Brown 17 and HC Blue 16, as well as Basic Yellow 87, Basic Orange 31 and Basic Red 51.

Preferred nonionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-Bis(2-Hydroxyethyl)-amino-2-nitrobenzene, 3-Nitro-4-(2 hydroxyethyl)aminophenol, 2-(2-hydroxyethyl)amino-4,6-dinitrophenol, 4-[(2-hydroxyethyl)amino]-3-nitro-1-methyl benzene, 1-Amino-4-(2-hydroxyethyl)amino-5-chloro-2-nitrobenzene, 4-Amino-3-nitrophenol, 1-(2'-ureidoethyl)amino-4-nitrobenzene, 2-[(4-Amino-2-nitrophenol)amino]benzoic acid, 6-Nitro-1,2,3,4-tetrahydrochinoxaline, 2-hydroxy-1,4-naphthoquinone, picramic acid and their salts, 2-Amino-6-chloro-4-nitrophenol, 4-(Ethylamino)-3-nitrobenzoic acid and 2-chlor-6-ethylamino-4-nitrophenol.

Moreover, partially-oxidizing dyes that occur in nature, such as Henna red, Henna neutral, Henna black, chamomile blossoms sandalwood, black tea, walnut, Cascara bark, sage, logwood, madder root, catechu and alkanna root, can also be used.

As contemplated herein, the cosmetic agent preferably contains a direct dye in a total amount of from about 0.001 to about 10 wt. %, preferably from about 0.01 to about 8 wt. %, more preferably from about 0.1 to about 5 wt. %, particularly from about 0.5 to about 2 wt. %, relative to the total weight of the cosmetic agent and/or composition used as contemplated herein (M1) in each case.

A further subject of the present disclosure is a package unit (kit-of-parts), comprising—separately packaged—the following:

a) at least one container (C1), containing an agent for oxidative hair coloring, which, relative to its weight in each case, contains the following:

from about 70-about 95 wt. %, preferably from about 78-about 91 wt. % water, at least one oxidation dye precursor, at least one alkalizing agent, at least one surfactant selected from anionic, zwitterionic and amphoteric surfactants and mixtures thereof, in a total amount of from about 0.1-about 2 wt. %, at least one crosslinked copolymer composed of acrylic acid and non-ethoxylated esters of acrylic acid with linear $C_{10}$-$C_{30}$ monoalcohols as monomers, wherein the crosslinked copolymer is present in a total amount of from about 0.05 to about 2 wt. %, at least one branched alkanol having a hydroxyl group and from about 10 to about 50 carbon atoms, preferably in a total amount of from about 0.1-about 5 wt. %, preferably from about 0.4-about 4 wt. %, more preferably from about 0.7-about 3 wt. %, particularly from about 1-about 2 wt. %, in each case relative to the weight of the agent, at least one linear, saturated 1-alkanol with a hydroxy group and from 8 to about 22 carbon atoms in a total amount of from about 0.1-about 1.5 wt. %, preferably from about 0.3-about 1 wt. %, particularly from about 0.5-about 0.8 wt. %, wherein no additional fat components with a melting point of about 35° C. or higher in addition to the obligatory ingredients mentioned above, no saturated and unsaturated alkane carboxylic acids with from 1 to about 50 carbon atoms and no oxidants are contained, and b) at least one container (C2), containing an oxidant preparation (M2), which contains from about 40-about 96 wt. %, preferably from about 70-about 93 wt. %, particularly from about 80-about 90 wt. %, and hydrogen peroxide in a total amount of from about 0.5 to about 23 wt. %, more preferably from about 2.5 to about 21 wt. %, particularly preferably from about 4 to about 20 wt. %, especially preferably from about 5 to about 18 wt. % and ideally from about 6 to about 12 wt. %, and has a pH value in the range of from about 2.0 to about 6.5, preferably from about 2.5 to about 5.5, particularly from about 2.8 to about 5.0, measured at 20° C. in each case, relative to the weight of the oxidant preparation (M2) in each case.

An additional subject of the present disclosure is a method for oxidative hair coloring that comprises the following method steps:

i) preparation of a cosmetic agent (M1) for oxidative hair coloring of keratinous fibers, containing from about 70-about 95 wt. % water, preferably from about 78-about 91 wt. % water, at least one oxidation dye precursor, at least one alkalizing agent, at least one surfactant selected from anionic, zwitterionic and amphoteric surfactants and mixtures thereof, in a total amount of from about 0.1-about 2 wt. %, at least one crosslinked copolymer composed of acrylic acid and non-ethoxylated esters of acrylic acid with linear $C_{10}$-$C_{30}$ monoalcohols as monomers, wherein the crosslinked copolymer is present in a total amount of from about 0.05 to about 2 wt. %, at least one branched alkanol having a hydroxyl group and from about 10 to about 50 carbon atoms, preferably in a total amount of from about 0.1-about 5 wt. %, preferably from about 0.4-about 4 wt. %, more preferably from about 0.7-about 3 wt. %, particularly from about 1-about 2 wt. %, in each case relative to the weight of the agent, at least one linear, saturated 1-alkanol with a hydroxy group and from 8 to about 22 carbon atoms in a total amount of from about 0.1-about 1.5 wt. %, preferably from about 0.3 about 1 wt. %, particularly from about 0.5-about 0.8 wt. %, wherein no additional fat components with a melting point of 35° C. or higher in addition to the obligatory ingredients mentioned above, no saturated and unsaturated alkane carboxylic acids with from 1 to about 50 carbon atoms and no oxidants are contained, ii) preparation of an oxidant preparation (M2), which contains from about 40-about 96 wt. %, preferably from about 70-about 93 wt. %, particularly from about 80-about 90 wt. %, and hydrogen peroxide in a total amount of from about 0.5 to about 23 wt. %, more preferably from about 2.5 to about 21 wt. %, particularly preferably from about 4 to about 20 wt. %, especially preferably from about 5 to about 18 wt. % and ideally from about 6 to about 12 wt. %, and has a pH value in the range of from about 2.0 to about 6.5, preferably from about 2.5 to about 5.5, particularly from about 2.8 to about 5.0, measured at 20° C. in each case, wherein the wt. % specifications are relative to the weight of the oxidant preparation (M2) in each case, wherein at least one cationic surfactant is optionally contained, iii) mixing of the cosmetic agent (M1) with the oxidant preparation (M2), preferably in a weight ratio (M1):(M2) in the range of from about 1:0.8 to about 1:2.5, preferably from about 1:1 to about 1:2, directly followed by iv) application of the mixture obtained in Step iii) onto the hair and leaving said mixture for a period of from about 1 to about 60 minutes, preferably from about 20 to about 45 minutes at room temperature and/or at least 30° C. on the hair, v) rinsing of the hair with water and/or a cleansing composition, and vi) optionally, application of a post-treatment shampoo onto the hair and, optionally rinsing, then drying.

For oxidative hair coloring methods, the one or multiple oxidative coloring precursors is mixed with an aqueous composition containing oxidants (M2) to form a coloring agent that is ready for application and applied to the hair immediately before the agent (M1) as contemplated herein is applied to the hair. The agent (M1) as contemplated herein and the composition containing oxidants (M2) are usually adjusted to each other so that, with a mixture ratio of 1 to 1, relative to the weight by part, an initial concentration of hydrogen peroxide of from about 0.5-about 12 wt. %, preferably from about 2-about 10 wt. %, particularly from about 3-about 6 wt. % hydrogen peroxide (calculated as 100% $H_2O_2$), relative to the weight of the application mixture in each case, is present in the final application mixture. However, it is equally possible to adjust the agent (M1) as contemplated herein and the composition containing oxidants (M2) to each other so that the concentrations necessary in the ready-to-use oxidation coloring agent (application mixture) are achieved by employing mixing ratios other than 1:1, for example by a weight-related mixture ratio of 1:2 or 1:3 or also 2:3.

Preferred weight-related mixture ratios (M1):(M2) as contemplated herein are in the range of from about 1:0.8 to about 1:2.5, wherein preference is given particularly to ratios in the range of from about 1:1 to about 1:2.

The term "room temperature" in the context of the present disclosure denotes the temperature in the room in which a person normally uses hair coloring agent, in other words, normally a bathroom or a hair salon in which a temperature in the range of from about 10-about 29° C. is prevalent.

The leaving of the hair coloring application mixture in method step iv) in the hair dyeing method as contemplated herein or preferred as contemplated herein can also take place at a temperature of at least 30° C., preferably at from about 30-about 60° C., particularly at from about 32-about 50° C., when the hair is heated, for example, with a heat hood or with a heat radiator.

The coloring kits as contemplated herein and coloring methods preferred as contemplated herein, as well as oxidant preparation (M2) preferably used as contemplated herein contains from about 40-about 96 wt. %, preferably from about 70-about 93 wt. %, particularly from about 80-about 90 wt. % water, relative to its weight in each case.

The oxidant preparation (M2) as contemplated herein and coloring kits preferred as contemplated herein, as well as in coloring methods as contemplated herein and preferred as contemplated herein additionally contain from about 0.5 to about 23 wt. %, preferably from about 2.5 to about 21 wt. %, more preferably from about 4 to about 20 wt. %, especially preferably from about 5 to about 18 wt. % and particularly from about 6 to about 12 wt. % hydrogen peroxide, relative to its weight in each case.

For stabilization of the hydrogen peroxide, the oxidant preparation (M2) has a pH value in the range of from about 2.0 to about 6.5, preferably from about 2.5-about 5.5, particularly from about 2.8 to about 5.0, measured at 20° C. in each case.

Cationic Surfactant in the Oxidant Preparation (M2)

The average viscosity of agents (M1) as contemplated herein in the range of from about 5000-about 40,000 mPas, preferably from about 6000-about 30,000 mPas, particularly from about 7500-about 20,000 mPas, measured at 20° C. with a rotation viscosimeter (Haake VT 550) with a rotation frequency of 7.2 $s^{-1}$ with measuring geometry SV in each case, is outstandingly suitable for the handling of this agent itself (production, dispensing in plastic bottles, metering for production of the mixture with the oxidant preparation). The oxidant preparation (M2) usually has a low viscosity in the range of from about 10-about 6000 mPas, preferably from about 200-about 5000 mPas, particularly from about 1000-about 4500 mPas, measured at 20° C. in each case. For application onto the hair, however, the application mixture should have a significantly higher viscosity so that it remains on the hair for the entire exposure time (in the range of from about 5-about 60 minutes, preferably from about 30-about 45 minutes) and does not drip. In this case, a distinction is made as to whether the application mixture is produced by shaking both compositions (M1) and (M2) in an application bottle from which the application mixture is applied to the hair immediately after mixing with the aid of an application nozzle as a bottle attachment (bottle application), or the application mixture is produced by stirring both compositions (M1) and (M2) in a bowl, from which the application mixture is applied to the hair immediately after mixing with a brush (brush application). Bottle application is particularly suitable for coloring agent that is sold in retail with a recommendation for application by the consumer themselves. Brush application is particularly suitable for coloring agent that is produced by the hairdresser in the salon and applied to the hair of the consumer.

Surprisingly, it was found that an application mixture with a viscosity especially suitable for brush application is achieved if the agent as contemplated herein or preferred as contemplated herein (M1) is mixed with an oxidant preparation (M2) that contains at least one cationic surfactant. During mixing, the interaction between the at least one crosslinked copolymer of acrylic acid and non-ethoxylated esters of acrylic acid with linear $C_{10}$-$C_{30}$ monoalcohols and the at least one cationic surfactant leads to the desired increase in viscosity. The pasty consistency of the application mixture achieved in the process provides optimal application characteristics, particularly for brush application. The application mixtures achieved in this manner, particularly the mixtures having a weight-related mixture ratio (M1):(M2) in the range of from about 1:0.8 to about 1:2.5, are preferably in the range of from about 1:1 to about 1:2, preferably having a viscosity in the range from about 20,000-about 100,000 mPas, preferably from about 30,000-about 80,000 mPas, particularly from about 45,000-about 70,000 mPas, measured at 20° C. in each case (Brookfield viscosimeter, rotation frequency of 4 rpm, spindle no. 5).

In another preferred embodiment of the present disclosure, the oxidant preparation (M2) used as contemplated herein contains at least one cationic surfactant, preferably in a total amount of from about 0.05-about 3 wt. %, preferably from about 0.1-about 1.5 wt. %, particularly from about 0.3-about 0.9 wt. %, relative to the weight of the oxidant preparation (M2) in each case.

The term cationic surfactants is understood to mean surfactants having one or multiple positive charges. Cationic surfactants contain positive charges only. Normally, these surfactants are composed of a hydrophobic part and a hydrophilic head group, wherein the hydrophobic part normally includes a hydrocarbon framework (e.g. including of one or two linear or branched alkyl chains) and the positive charge(s) in the hydrophilic head group are localized. Cationic surfactants adsorb on boundary surfaces and aggregate in an aqueous solution above the critical micelle formation concentration to form positively charged micelles.

As contemplated herein, preference is given to cationic surfactants of the type of quaternary ammonium compounds, esterquats and alkyl amidoamines. Preferred quaternary ammonium compounds are ammonium halides, such as alkyltrimethylammonium chlorides, dialkyldimethylammonium chlorides, trialkylmethylammonium chlorides, and the imidazolium compounds known under the INCI designations quaternium-27 and quaternium-83. Additional preferred quaternary ammonium compounds are tetraalkylammonium salts, particularly known under the INCI designation the quaternium-52, a poly(oxy-1,2-ethanediyl), ((octadecylnitrilio)tri-2,1-ethanediyl)tris(hydroxy)phosphate (1:1)-salt, which has the general structural formula (III), wherein x+y+z=10:

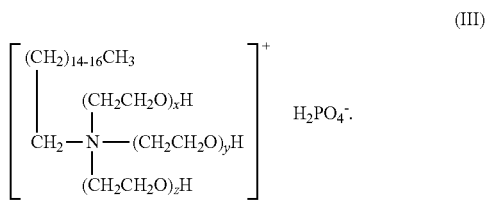

(III)

The long alkyl chains of the aforementioned surfactants preferably have from 10 to about 22, particularly from 12 to 18 carbon atoms. Particular preference is given to behenyltrimethylammonium chloride, stearyltrimethylammonium chloride and cetyl trimethyl ammonium chloride, wherein stearyltrimethylammonium chloride is preferred in particular. Further suitable cationic surfactants as contemplated herein are quaternized protein hydolysates. Alkylamidoamines are usually produced through the amidation of natural or synthetic fatty acids and fatty acid molecules with dialkylaminoamines. As contemplated herein, Tegoamid® S 18 (stearamidopropyldimethylamine) is a suitable compound from this group of substances. Esterquats are substances containing both at least one ester function and at least quaternary ammonium group as the structural element. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines. Such products are sold under the trade names Stepantex, Dehyquart and Armocare.

$C_{10}$-$C_{22}$-alkyltrimethylammonium chlorides have been demonstrated to be especially well-suited in regard to optimal application characteristics and optimal dying results. Therefore, especially preferred oxidant preparations (M2) used as contemplated herein are exemplified in that they contain at least one cationic surfactant in a total amount of from about 0.05-about 3 wt. %, preferably from about 0.1-about 1.5 wt. %, particularly from about 0.3-about 0.9 wt. %, relative to the weight of the oxidant preparation (M2) in each case, wherein at least one surfactant selected from $C_{10}$-$C_{22}$-alkyltrimethylammonium chlorides, particularly selected from behenyltrimethylammonium chloride, stearyltrimethylammonium chloride and cetyltrimethylammonium chloride, as well as mixtures of surfactants, is included. Particularly preferred oxidant preparations (M2) used as contemplated herein contain stearyltrimethylammonium chloride in a total amount of from about 0.05-about 3 wt. %, preferably from about 0.1-about 1.5 wt. %, particularly from about 0.3-about 0.9 wt. %, relative to the weight of the oxidant preparation (M2) in each case.

A further package unit (kit-of-parts) preferred as contemplated herein is exemplified in that the oxidant agent preparation (M2) contains at least one cationic surfactant, preferably in a total amount of from about 0.05-about 3 wt. %, more preferably from about 0.1-about 1.5 wt. %, particularly from about 0.3-about 0.9 wt. %, relative to the weight of the oxidant preparation (M2) in each case, but does not contain a polymer having a degree of polymerization of at least about 200 or polymer having a molecular weight of about 10,000 daltons or higher.

It was discovered that the thickening with the aid of the interaction between the copolymer in the agent as contemplated herein and the cationic surfactant in the oxidant preparation (M2) is sufficient and cannot be further increased or even impaired in its application properties by the presence of a polymer having a degree of polymerization of at least about 200 or a polymer having a molecular weight of about 10,000 daltons or higher.

A further package unit (kit of parts) preferred as contemplated herein is exemplified in that the oxidant preparation (M2) contains at least one cationic surfactant, which is preferably selected from stearyltrimethylammonium chloride, in a total amount of from about 0.05-about 3 wt. %, preferably from about 0.1-about 1.5 wt. %. %, particularly from about 0.3-about 0.9 wt. %, relative to the weight of the oxidant preparation (M2) in each case, but does not contain a polymer having a degree of polymerization of at least about 200 or a polymer having a molecular weight of about 10,000 daltons or higher.

A preferred method for oxidative hair coloring as contemplated herein is exemplified in that the oxidant agent preparation (M2) contains at least one cationic surfactant, preferably in a total amount of from about 0.05-about 3 wt. %, more preferably from about 0.1-about 1.5 wt. %, particularly from about 0.3-about 0.9 wt. %, relative to the weight of the oxidant preparation (M2) in each case, but does not contain a polymer having a degree of polymerization of at least about 200 or polymer having a molecular weight of about 10,000 daltons or higher.

A further method for oxidative hair coloring preferred as contemplated herein is exemplified in that the oxidant agent preparation (M2) contains at least one cationic surfactant, which is preferably selected from stearyltrimethylammonium chloride in a total amount of from about 0.05-about 3 wt. %, more preferably from about 0.1-about 1.5 wt. %, particularly from about 0.3-about 0.9 wt. %, relative to the weight of the oxidant preparation (M2) in each case, but does not contain a polymer having a degree of polymerization of at least about 200 or polymer having a molecular weight of about 10,000 daltons or higher.

Surprisingly, it has been found that an application mixture with a viscosity that is particularly suitable for bottle application is achieved if the agent (M1) as contemplated herein or preferred as contemplated herein is mixed with an oxidant preparation (M2) having at least one copolymer selected from crosslinked acrylic acid/acrylic acid-C1-C6 alkylester-copolymers and crosslinked methacrylic acid/acrylic acid-C1-C6-alkylester-copolymers, preferably in a total amount of from about 0.1-about 7 wt. %, more preferably from about 0.5-about 6 wt. %, particularly from about 1-about 4.5 wt. %, relative to the weight of the oxidant preparation (M2) in each case. The mixing of the agent as contemplated herein or preferred as contemplated herein with such an oxidant preparation (M2) achieves the desired increase of viscosity. The medium-viscosity consistency of the application mixture achieved in the process provides optimal application characteristics, particularly for bottle application. The application mixtures achieved in this manner, particularly the mixtures having weight-related mixture ratios (M1):(M2) in the range of from about 1:0.8 to about 1:2.5, are preferably in the range of from about 1:1 to about 1:2, preferably having a viscosity in the range from about 10,000 about 50,000 mPas, preferably from about 15,000-about 30,000 mPas, more preferably from about 15,000-about 30,000 mPas, particularly from about 18,000-about 25,000 mPas, measured at 20° C. in each case (Brookfield viscosimeter, rotation frequency of 4 rpm, spindle no. 5).

A further package unit (kit of parts) preferred as contemplated herein is exemplified in that the oxidant preparation (M2) contains at least one copolymer selected from crosslinked acrylic acid/acrylic acid-C1-C6 alkylester-copolymers and crosslinked methacrylic acid/acrylic acid-C1-C6-alkylester-copolymers, preferably in a total amount of from about 0.1-about 7 wt. %, more preferably from about 0.5-about 6 wt. %, particularly from about 1-about 4.5 wt. %, relative to the weight of the oxidant preparation (M2) in each case, and preferably containing no cationic surfactants.

A further method preferred as contemplated herein for oxidative hair coloring is exemplified in that the oxidant preparation (M2) contains at least one copolymer selected from crosslinked acrylic acid/acrylic acid-C1-C6 alkylester-copolymers and crosslinked methacrylic acid/acrylic acid-C1-C6-alkylester-copolymers, preferably in a total amount of from about 0.1-about 7 wt. %, more preferably from about 0.5-about 6 wt. %, particularly from about 1-about 4.5 wt. %, relative to the weight of the oxidant preparation (M2) in each case, and preferably containing no cationic surfactants.

Preference is given to crosslinked copolymers of this type selected from—crosslinked in each case—methacrylic acid/methacrylate-, methacrylic acid/ethylacrylate-, methacrylic acid/propylacrylate-, methacrylic acid/butylacrylate-, methacrylic acid/pentylacrylate-, methacrylic acid/hexylacrylate-, acrylic acid/methylacrylate-, acrylic acid/ethylacrylate-, acrylic acid/propylacrylate-, acrylic acid/butylacrylate-, acrylic acid/pentylacrylate- and acrylic acid/hexylacrylate-copolymers and mixtures thereof.

A further preferred package unit (kit of parts) as contemplated herein is exemplified in that the oxidant preparation (M2) contains at least one crosslinked copolymer selected from—crosslinked in each case—methacrylic acid/methacrylate-, methacrylic acid/ethylacrylate-, methacrylic acid/propylacrylate-, methacrylic acid/butylacrylate-, methacrylic acid/pentylacrylate-, methacrylic acid/hexylacrylate-, acrylic acid/methylacrylate-, acrylic acid/ethylacrylate-, acrylic acid/propylacrylate-, acrylic acid/butylacrylate-, acrylic acid/pentylacrylate- and acrylic acid/hexylacrylate-copolymers and mixtures thereof, in a total amount of from about 0.1-about 7 wt. %, more preferably from about 0.5-about 6 wt. %, particularly from about 1-about 4.5 wt. %, relative to the weight of the oxidant preparation (M2) in each case, and preferably containing no cationic surfactants.

A further preferred method for oxidative hair coloring as contemplated herein is exemplified in that the oxidant preparation (M2) contains at least one crosslinked copolymer selected from—crosslinked in each case—methacrylic acid/methacrylate-, methacrylic acid/ethylacrylate-, methacrylic acid/propylacrylate-, methacrylic acid/butylacrylate-, methacrylic acid/pentylacrylate-, methacrylic acid/hexylacrylate-, acrylic acid/methylacrylate-, acrylic acid/ethylacrylate-, acrylic acid/propylacrylate-, acrylic acid/butylacrylate-, acrylic acid/pentylacrylate- and acrylic acid/hexylacrylate-copolymers and mixtures thereof, in a total amount of from about 0.1-about 7 wt. %, more preferably from about 0.5-about 6 wt. %, particularly from about 1-about 4.5 wt. %, relative to the weight of the oxidant preparation (M2) in each case, and preferably containing no cationic surfactants.

The oxidant preparations (M2) as contemplated herein and preferably used as contemplated herein can also contain stabilizers, particularly complexing agents and pH buffer substances.

In another preferred embodiment of the present disclosure, the oxidant preparation (M2) used as contemplated herein contains at least one oil in a total amount of from about 0.2-about 50 wt. %, preferably from about 2-about 40 wt. %, particularly from about 8-about 30 wt. %, especially from about 15-about 25 wt. %, relative to the weight of the oxidant preparation (M2) in each case.

Particular preference is given to an embodiment of the present disclosure wherein the oxidant preparation (M2) used as contemplated herein contains no cationic surfactants and at least one oil in a total amount of from about 0.2-about 50 wt. %, preferably from about 2-about 40 wt. %, particularly from about 8-about 30 wt. %, especially from about 15-about 25 wt. %, relative to the weight of the oxidant preparation (M2) in each case.

The at least one oil contained in the oxidant preparation (M2) in a total amount of from about 0.2-about 50 wt. % relative to the weight of the preparation (M2) water-in-oil emulsion containing sodium polyacrylate is preferably selected from natural and synthetic hydrocarbons, particularly preferably from mineral oil, paraffin oils, $C_{18}$-$C_{30}$-isoparaffins, particularly isoeicosane, polyisobutenes and polydecenes, $C_8$-$C_{16}$ isoparaffins, and 1,3-di-(2-ethylhexyl)-cyclohexane; the benzoic esters of linear or branched $C_{8-22}$-alkanols; triglycerides of linear or branched, saturated or unsaturated, optionally hydroxylated $C_{8-30}$-fatty acids, in particular natural oils; the dicarboxylic acid esters of linear or branched $C_2$-$C_{10}$-alkanols; the esters of the linear or branched saturated or unsaturated fatty alcohols having from 2-about 30 carbon atoms with linear or branched saturated or unsaturated fatty alcohols having from 2-about 30 carbon atoms, branched saturated or unsaturated fatty acids having from 2-about 30 carbon atoms, which can be hydroxylated; the addition products of from 1 to 5 propylene oxide units to mono- or polyhydric $C_{8-22}$-alkanols; the $C_8$-$C_{22}$-fatty alcohol esters of monohydric or polyhydric $C_2$-$C_7$-hydroxycarboxylic acids; the symmetrical, asymmetric or cyclic esters of carbonic acid with $C_{3-22}$-alkanols, $C_{3-22}$-alkane diols or $C_{3-22}$-alkane triols; the esters of dimeric unsaturated $C_{12}$-

$C_{22}$-fatty acids (dimer fatty acids) with monovalent linear, branched or cyclic $C_2$-$C_{18}$-alkanols or with polyvalent linear or branched $C_2$-$C_6$-alkanols; silicone oils and mixtures of the aforementioned substances. In this context, as contemplated herein particularly preferred oils are selected from paraffin oils and the esters of linear or branched saturated or unsaturated fatty alcohols with from 2-about 30 carbon atoms with linear or branched saturated or unsaturated fatty acids with from 2-about 30 carbon atoms that can be hydroxylated, as well as mixtures thereof, with particular preference being given to oils selected from paraffin oil, isopropyl palmitate and isopropyl myristate.

In a further preferred embodiment of the present disclosure, the oxidant preparation (M2) used as contemplated herein contains at least on surfactant selected from anionic surfactants and nonionic surfactants and mixtures thereof, in a total amount of from about 0.05-about 2 wt. %, preferably from about 0.3-about 1.5 wt. %, and at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-about 5 wt. %, preferably from about 1.5-about 4 wt. %, wherein all quantitative data is relative to the weight of the oxidant preparation (M2), and wherein the preparation (M2) does not contain any cationic surfactants, oils, polymers having a degree of polymerization of at least about 200 or polymers having a molecular weight of about 10000 daltons or higher.

A further preferred package unit (kit of parts) as contemplated herein and a further hair coloring method preferred as contemplated herein are each exemplified in that the oxidant preparation (M2) used as contemplated herein contains at least on surfactant selected from anionic surfactants and nonionic surfactants and mixtures thereof, in a total amount of from about 0.05-about 2 wt. %, preferably from about 0.3-about 1.5 wt. %, and at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-about 5 wt. %, preferably from about 1.5-about 4 wt. %, relative to the weight of the oxidant preparation (M2) in each case.

A further preferred package unit (kit of parts) as contemplated herein and a preferred hair coloring method preferred as contemplated herein are each exemplified in that the oxidant preparation (M2) used as contemplated herein contains at least on surfactant selected from anionic surfactants and nonionic surfactants and mixtures thereof, in a total amount of from about 0.05-about 2 wt. %, preferably from about 0.3-about 1.5 wt. %, and at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-about 5 wt. %, preferably from about 1.5-about 4 wt. %, relative to the weight of the oxidant preparation (M2) in each case, bot do no not contain any cationic surfactants, oils, polymers having a degree of polymerization of at least about 200 or polymers having a molecular weight of about 10000 daltons or higher.

It was discovered that the thickening with the aid of the interaction between the copolymer in the agent as contemplated herein and aforementioned surfactant/1-alkanol mixture in the oxidant preparation (M2) is sufficient and cannot be further increased or even impaired in its application properties by the presence of a polymer having a degree of polymerization of at least about 200 or a polymer having a molecular weight of about 10,000 daltons or higher.

A further preferred package unit (kit of parts) as contemplated herein and a further hair coloring method preferred as contemplated herein are each exemplified in that the oxidant preparation (M2) used as contemplated herein contains at least on surfactant selected from anionic surfactants and nonionic surfactants and mixtures thereof, in a total amount of from about 0.05-about 2 wt. %, preferably from about 0.3-about 1.5 wt. %, at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-about 5 wt. %, preferably from about 1.5-about 4 wt. %, and at least one oil in a total amount of from about 0.2-about 50 wt. %, preferably from about 2-about 40 wt. %, more preferably from about 8-about 30 wt. %, particularly from about 15-about 25 wt. %, relative to the weight of the oxidant preparation (M2) in each case.

A further preferred package unit (kit of parts) as contemplated herein and a preferred hair coloring method preferred as contemplated herein are each exemplified in that the oxidant preparation (M2) used as contemplated herein contains at least on surfactant selected from anionic surfactants and nonionic surfactants and mixtures thereof, in a total amount of from about 0.05-about 2 wt. %, preferably from about 0.3-about 1.5 wt. %, and at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-about 5 wt. %, preferably from about 1.5-about 4 wt. %, and at least one oil in a total amount of from about 0.2-about 50 wt. %, preferably from about 2-about 40 wt. %, more preferably from about 8-about 30 wt. %, particularly from about 15-about 25 wt. % relative to the weight of the oxidant preparation (M2) in each case, but do no not contain any polymers having a degree of polymerization of at least about 200 or polymers having a molecular weight of about 10,000 daltons or higher.

All anionic surfactants discussed above for the agent (M1) as contemplated herein are suitable as anionic surfactants for the oxidant preparations (M2) used as contemplated herein.

Suitable for use as nonionic surfactants for the oxidant preparations (M2) used as contemplated herein are all non-ionic surfactant substances suitable for use on the human body, which have at least one water-solubilizing, nonionic group, in particular a polyethylene glycol ether group having at least 2 ethylene oxide units, a glycoside group, in particular a glucose or methylglucose group, a polyglycoside group having on average more than one glycoside unit, a polyglycerol group having at least two glycerol units, a sorbitan group, an amide group or a plurality of different groups of this type, for example a sorbitan group and a polyethylene glycol ether group, and a lipophilic alkyl group having from 8 to about 30 C atoms, preferably from 10 to about 24 C atoms. Particularly preferred non-ionic surfactants are selected from 7-about 80 mol of ethylene oxide per mole of ethoxylated castor oil, ethoxylated $C_8$-$C_{30}$-alkanols with from 4-about 100 mol of ethylene oxide per mole, ethoxylated $C_8$-$C_{30}$-carboxylic acids with from 5-about 30 mol of ethylene oxide per mole, with from 4-about 50 mol of ethylene oxide per mole of ethoxylated sorbitan monoesters of linear saturated and unsaturated $C_{12}$-$C_{30}$-carboxylic acids, which can be hydroxylated, in particular those of myristic acid, palmitic acid, stearic acid or mixtures of these fatty acids, alkyl mono- and oligoglycosides having from 8 to about 22 carbon atoms in the alkyl radical and their ethoxylated analogs, and mixtures of the aforementioned substances.

The ethoxylated $C_8$-$C_{30}$-alkanols have the formula $R^1O(CH_2CH_2O)_nH$, wherein $R^1$ denotes a linear or branched alkyl and/or alkenyl radical with from 8-about 30 carbon atoms and n, the average number of ethylene oxide units per molecule, for integers from 4-about 100, preferably from 6-about 30, particularly from 12 to about 20 mol of ethylene oxide on 1 mol of alkanol, which is preferably selected from caprylic alcohol, 2-ethylhexylalcohol, capric alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, and technical mixtures thereof. Adducts of from 10 to about 100 mol of ethylene oxide with technical fatty alcohols having from 12 to 18 carbon atoms are also known, such as coconut, palm, palm kernel or tallow fatty alcohol, are suitable. Particular preference is given to trideceth-6, isotrideceth-6, undeceth-6, myreth-6, laureth-10, laureth-12, laureth-15, laureth-20, laureth-30, myreth-10, myreth-12, myreth-15, myreth-20, myreth-30, ceteth-10, ceteth-12, ceteth-15, ceteth-20, ceteth-30, steareth-10, steareth-12 steareth-15, steareth-20, steareth-30, oleth-10, oleth-12, oleth-15, oleth-20, oleth-30, ceteareth-10, ceteareth-15, ceteareth-12, ceteareth-15, ceteareth-20, ceteareth-30 and coceth-10, coceth-12, coceth-15, coceth-20 and coceth-30; with preference given in particular to ceteth-10, ceteth-12, ceteth-15, ceteth-30, steareth-10, steareth-12, steareth-15, steareth-20 and steareth-30 and mixtures thereof.

The ethoxylated $C_8$-$C_{30}$-carboxylic acids have the formula $R^1O(CH_2CH_2O)_nH$, wherein $R^1O$ denotes a linear or branched saturated or unsaturated alkenyl radical with from 8-about 30 carbon atoms and n, the average number of ethylene oxide units per molecule, for integers from 5-about 30, preferably from 6-about 20, particularly from 6 to 12 mol of ethylene oxide on 1 mol of $C_8$-$C_{30}$-carboxylic acid, which is preferably selected from, capric acid, 2-ethylhexanoic acid, capric acid, lauric acid, isotridecanoic acid, myristic acid, cetyl acid, palmitoleic acid, stearic acid, isostearic acid, oleic acid, elaidic acid, petroselinic acid, arachidic acid, gadoleic acid, behenic acid, erucic acid and brassidic acid, and technical mixtures thereof. Adducts of from 5-about 30 mol, preferably from 6-about 20 mol, particularly from 6-12 mol of ethylene oxide with technical fatty acids having from 12 to 18 carbon atoms, such as coconut, palm, palm kernel or tallow fatty alcohol, are suitable.

With respect to the cosmetic agent (M1) in container C1 and the oxidant preparation (M2) in container C2 of the kits as contemplated herein and preferred as contemplated herein, the statement made about cosmetic agents as contemplated herein apply mutatis mutandis.

With respect to the cosmetic agent (M1) in container C1 of the methods for oxidative hair coloring as contemplated herein and preferred as contemplated herein, the statements made about the cosmetic agents as contemplated herein and preferred as contemplated herein apply mutatis mutandis.

With respect to the oxidant preparation (M2) in container C2 of the methods for oxidative hair coloring as contemplated herein and preferred as contemplated herein, the statements made about the oxidative hair coloring as contemplated herein and preferred as contemplated herein apply mutatis mutandis.

The container wall of container C1 and C2 is preferably made of a polyolefin, such as polypropylene (PP), high density polyethylene (HDPE), medium density polyethylene (MDPE), low density polyethylene (LDPE), linear low density polyethylene (LLDPE). Polyethylene is particularly suitable, in particular high density polyethylene (HDPE).

For improved intermixing of (M1) and (M2), it is preferred that the container (C2) containing the oxidizing agent preparation (M2) is designed as a bottle and has a re-closable opening, such as, a snap-action or screw-type closure. This enables easier addition of color-changing agent from container (C1), which is preferably designed as a bottle made of a polyolefin.

The following examples are intended to explain the subject matter of the present disclosure without having any limiting effect.

EXAMPLES

TABLE 1

Coloring cream gel for oxidative hair coloring

| Ingredient | Initial weight (wt. %) |
|---|---|
| Monoethanolamine (2-aminoethan-1-ol) | 1.65 |
| Ammonium hydroxide | 4.65 |
| Acrylates/$C_{10-30}$ alkyl acrylate crosspolymer | 0.40 |
| Sodium polyacrylate* | (active content) 1.00 |
| Mineral oil | 0.70 |
| Trideceth-6 | 0.10 |
| Sodium laureth sulfate | 0.80 |
| L-Serin | 0.08 |
| 2-octyldodecanol | 2.00 |
| Coconut fatty alcohol** | 0.80 |
| Sodium sulfate | 0.60 |
| Tetrasodium EDTA | 0.30 |
| Ascorbic acid | 0.15 |
| Toluene-2.5-diamin sulfate | 3.89 |
| Resorcin | 0.97 |
| m-aminophenol | 0.19 |
| 4-chlororesorcin | 0.68 |
| 2.4-diaminophenoxyethanol HCl | 0.70 |
| Water | ad 100.00 |

*Sodium polyacrylate, supplied in a water-in-mineral oil emulsion with trideceth-6 as an emulsifier
**Raw material "Synative AL T" from BASF; INCI: Coconut alcohol; C10 and shorter: max. 3 wt. %, C12: from about 48-about 58 wt. %, C14: from about 18-about 24 wt. %, C16: from about 8-about 12 wt. %, C18: from about 11-about 15 wt. %, C20: max. 1 wt. %

Viscosity: 15,000 mPas, measured at 20° C. with a rotation viscosimeter (Haake VT 550) with a rotation frequency of 7.2 s$^{-1}$ with measurement geometry SV

TABLE 2

Developers containing oxidant for the color cream from Table 1

| Ingredient | Initial weight (wt. %) |
|---|---|
| Sodium benzoate | 0.04 |
| Dipicolinic acid (2.6-dicarboxypyridine) | 0.10 |
| Di-sodium pyrophosphate | 0.10 |
| Potassium hydroxide | 0.10 |
| 1,2-propanediol | 1.00 |
| Etidronic acid | 0.15 |
| Paraffin oil | 0.30 |
| Stearyltrimethylammonium chloride | 0.30 |
| Cetearyl alcohol | 3.40 |
| Ceteareth-20 | 1.00 |

TABLE 2-continued

Developers containing oxidant for the color cream from Table 1

| Ingredient | Initial weight (wt. %) |
|---|---|
| Hydrogen peroxide | 6.00 |
| Water | ad 100.00 |

Viscosity: 4500 mPas, measured at 20° C. with a rotation viscosimeter (Haake VT 550) with a rotation frequency of 4 rpm with measurement geometry MV II

TABLE 3

Developers containing oxidant for the color cream from Table 1

| Ingredient | Initial weight (wt. %) |
|---|---|
| Sodium hydroxide | 0.40 |
| Dipicolinic acid (2.6-dicarboxypyridine) | 0.10 |
| Di-sodium pyrophosphate | 0.03 |
| Etidronic acid | 0.15 |
| Mixture of crosslinked (meth)acrylic acid/acrylic acid-C1-C6-alkylester-copolymers (e.g. Aculyn 33A) | 4.20 |
| Sodium laureth(2)sulfate | 0.50 |
| Hydrogen peroxide | 6.00 |
| Water | ad 100.00 |

* Aculyn 33A: aqueous dispersion of acrylate copolymer (mixture of crosslinked (meth) acrylic acid/acrylic acid-C1-C6-alkylester copolymers); 28 wt. % polymer content (active substance)

Viscosity: 200 mPas, measured at 20° C. with a Brookfield rotation viscosimeter at a rotation frequency of 20 rpm with spindle 2

TABLE 4

Developers containing oxidant for the color cream from Table 1

| Ingredient | Initial weight (wt. %) |
|---|---|
| Sodium benzoate | 0.04 |
| Dipicolinic acid (2.6-dicarboxypyridine) | 0.10 |
| Di-sodium pyrophosphate | 0.10 |
| Potassium hydroxide | 0.12 |
| Etidronic acid | 0.15 |
| Paraffin oil | 20.00 |
| Sodium cetearyl sulfate | 0.36 |
| Cetearyl alcohol | 3.50 |
| PEG-40 Castor Oil | 0.70 |
| Hydrogen peroxide | 6.00 |
| Water | ad 100.00 |

Viscosity: 7500 mPas, measured at 20° C. with a rotation viscosimeter (Haake VT 550) with a rotation frequency of 4 rpm with measurement geometry MV II

TABLE 5

Developers containing oxidant for the color cream from Table 1

| Ingredient | Initial weight (wt. %) |
|---|---|
| Sodium benzoate | 0.04 |
| Di-sodium pyrophosphate | 0.10 |
| Potassium hydroxide | 0.12 |
| Etidronic acid | 0.15 |
| Sodium cetearyl sulfate | 0.20 |
| Cetearyl alcohol | 1.70 |
| PEG-40 Castor Oil | 0.40 |
| Hydrogen peroxide | 6.00 |
| Water | ad 100.00 |

Viscosity: 2500 mPas, measured at 20° C. with a rotation viscosimeter (Haake VT 550) with a rotation frequency of 4 rpm with measurement geometry MV II Production of the Application Mixtures and Dyeing of Hair Coloring gel and the developer according to Table 6 were mixed with one another homogeneously. The application mixtures obtained in this way were each applied immediately after production on strands of human hair (natural white hair, Kerling company) (liquor ratio 4 grams of application mixture per gram of hair) and left on the hair for an exposure time of 30 minutes at room temperature (22° C.). Then the strands were rinsed out and dried with a hand towel.

TABLE 6

Production of the application mixtures for the dyeing of hair

| Alkaline dye cream (M1) | Developer (M2) | Weight ratio (M1):(M2) | Viscosity of the application mixture [mPas]* |
|---|---|---|---|
| according to Table 1 | according to Table 2 | 1:2 | 52,000 |
| according to Table 1 | according to Table 2 | 1:1 | 67,000 |
| according to Table 1 | according to Table 3 | 1:2 | 22,000 |
| according to Table 1 | according to Table 3 | 1:1 | 18,000 |
| according to Table 1 | according to Table 4 | 1:2 | 70,000 |
| according to Table 1 | according to Table 4 | 1:1 | 80,000 |
| according to Table 1 | according to Table 5 | 1:2 | 24,000 |
| according to Table 1 | according to Table 5 | 1:1 | 34,000 |

*Viscosity measured at 20° C. with a Brookfield rotation viscosimeter at a rotation frequency of 4 rpm with spindle 5

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Agent for oxidative hair coloring, comprising, relative to the weight of the agent,
    from about 70-about 95 wt. % water,
    at least one oxidation dye precursor,
    at least one alkalizing agent,
    at least one surfactant selected from anionic, zwitterionic and amphoteric surfactants and mixtures thereof, in a total amount of from about 0.1-about 2 wt. %,
    at least one crosslinked copolymer, composed of acrylic acid and non-ethoxylated esters of acrylic acid with linear $C_{10}$-$C_{30}$-monoalcohols as monomers in a total amount of from about 0.05-about 2 wt. %, at least one branched alkanol having a hydroxyl group and from about 10 to about 50 carbon atoms, at least one linear, saturated 1-alkanol with a hydroxy group and from about 8 to about 22 carbon atoms in a total amount of from about 0.1-about 1.5 wt. %, wherein no additional fat components with a melting point of 35° C. or higher in addition to the obligatory ingredients mentioned above, no saturated and unsaturated alkane carboxylic acids with from about 1 to about 50 carbon atoms and no oxidants are included in the agent, wherein sodium polyacrylate is present in the agent.

2. Agent according to claim 1, wherein the alkalizing agent is selected from the group of ammonia, basic amino acids, alkali metal hydroxides, alkanolamines, alkali metal metasilicates, alkali metal phosphates and mixtures thereof.

3. Agent according to claim 1, wherein the at least one anionic or zwitterionic surfactant is present and is selected from $C_8$-$C_{20}$ alkyl sulfates, $C_8$-$C_{20}$ alkyl ether sulfates and $C_8$-$C_{20}$ ether carboxylic acids, each having from about 8 to about 20 carbon atoms in the alkyl group and from 0 to about 12 ethylene oxide groups in the molecule, wherein the at least one anionic or zwitterionic surfactant is furthermore selected from coconut acylaminopropyl dimethyl ammonium glycinate, and from mixtures of these surfactants.

4. Agent according to claim 1, wherein the at least one crosslinked copolymer is selected from acrylic acid and non-ethoxylated esters of acrylic acid with linear $C_{10}$-$C_{30}$-monoalcohols.

5. Agent according to claim 1, having a pH value in the range of from about 8 to about 12, measured at 20° C.

6. Agent according to claim 1, having a viscosity in the range of from about 5000 to about 40,000 mPas, measured at 20° C. using a rotational viscometer (Haake VT 550) at a rotational frequency of 7.2 $s^{-1}$ with measurement geometry SV.

7. Agent according to claim 1, wherein the at least one branched alcohol with a hydroxy group and from about 10 to about 50 carbon atoms is selected from 2-hexyldecanol, 2-ocyltdodecanol, 2-ethylhexylalcohol, isostearylalcohol, and mixtures thereof.

8. Package unit (kit-of-parts), comprising—separately packaged—
a) at least one container (C1), comprising an agent for oxidative hair coloring according to claim 1, and
b) at least one container (C2), comprising an oxidant preparation (M2), which comprises water in a total amount of from about 40 to about 96 wt. %, and hydrogen peroxide in a total amount of from about 0.5 to about 23 wt. %, and has a pH value in the range of from about 2.0 to about 6.5, measured at 20° C., wherein the amounts are relative to the weight of the oxidant preparation (M2).

9. Package unit (kit of parts) according to claim 8, wherein the oxidant preparation (M2) comprises at least one cationic surfactant.

10. Package unit (kit of parts) according to claim 9, wherein the oxidant preparation (M2) does not contain any polymers having a degree of polymerization of at least about 200 or polymers having a molecular weight of about 10,000 daltons or higher.

11. Package unit (kit of parts) according to claim 8, wherein the oxidant preparation (M2) comprises at least one copolymer selected from crosslinked acrylic acid/acrylic acid-C1-C6 alkylester-copolymers and crosslinked methacrylic acid/acrylic acid-C1-C6-alkylester-copolymers, and contains no cationic surfactants.

12. Package unit (kit of parts) according to claim 8, wherein the oxidant preparation (M2) comprises at least one oil in a total amount of from about 0.2 to about 50 wt. %, relative to the weight of the oxidant preparation (M2), and does not contain any cationic surfactants.

13. Method for oxidative hair coloring comprising the following method steps:
i) Provision of a cosmetic agent for oxidative hair coloring (M1) according to claim 1,
ii) Preparation of an oxidant preparation (M2), comprising water in a total amount of from about 40 to about 96 wt. %, hydrogen peroxide in a total amount of from about 0.5 to about 23 wt. %, and has a pH value in the range of from about 2.0 to about 6.5, measured at 20° C., wherein the wt. % is relative to the weight of oxidant preparation (M2), wherein either at least one cationic surfactant or at least one copolymer, selected from crosslinked acrylic acid/acrylic acid-c1-c6-alkyl ester copolymers and crosslinked methacrylic acid/acrylic acid-c1-c6-alkyl ester copolymers is present,
iii) mixing of the cosmetic agent (M1) with the oxidant preparation (M2), in a weight ratio (M1):(M2) in the range of from about 1:0.8 to about 1:2.5, directly followed by
iv) application of the mixture obtained in Step iii) onto the hair and leaving said mixture for a period of from about 1 to about 60 minutes on the hair,
v) rinsing of the hair with water and/or a cleansing composition, and
vi) optionally, application of a post-treatment shampoo onto the hair and, optionally rinsing, then drying.

14. Method for oxidative hair coloring according to claim 13, wherein the oxidant agent preparation (M2) comprises at least one cationic surfactant in a total amount of from about 0.05 to about 3 wt. %, relative to the weight of the oxidant preparation (M2), and does not contain a polymer having a degree of polymerization of at least about 200 or polymer having a molecular weight of about 10,000 daltons or higher.

15. Method for oxidative hair coloring according to claim 13, wherein the oxidant preparation M2 comprises at least one copolymer selected from crosslinked acrylic acid/acrylic acid-C1-C6-alkylester-copolymers and crosslinked methacrylic acid/acrylic acid-C1-C6-alkylester-copolymers, in a total amount of from about 0.1 to about 7 wt. %, relative to the weight of the oxidant preparation (M2) and does not comprise any cationic surfactants.

16. Agent according to claim 1, wherein water is present in an amount of from about 78 to about 91 wt. % relative to the weight of the agent.

17. Agent according to claim 1, wherein the at least one branched alkanol having the hydroxyl group is present in a total amount of from about 0.1 to about 5 wt. % relative to the weight of the agent.

18. Agent according to claim 1, wherein the sodium polyacrylate has a mass-average molar mass $M_w$ in the range from about 1,000,000 to about 20,000,000 daltons.

19. Agent according to claim 1, wherein:
water is present in an amount of from about 78 to about 91 wt. % relative to the weight of the agent,
the at least one branched alkanol having the hydroxyl group is present in a total amount of from about 0.1 to about 5 wt. % relative to the weight of the agent,
the sodium polyacrylate has a mass-average molar mass $M_w$ in the range from about 6,000,000 to about 15,000, 000 daltons and is present in a total amount of from about 0.1 to about 1.5 wt. %, wherein the at least one anionic or zwitterionic surfactant is present and is included in a total amount of from about 0.3 to about 1.5 wt. %, wherein all amounts are relative to the weight of the agent.

* * * * *